United States Patent
Richman

(10) Patent No.: US 7,741,513 B2
(45) Date of Patent: Jun. 22, 2010

(54) THIOACIDS AND THIOACID SALTS FOR DETERMINING THE ENANTIOMERIC EXCESS OF CHIRAL COMPOUNDS CONTAINING AN ELECTROPHILIC CARBON CENTER

(76) Inventor: Jack E. Richman, 6710 Stillwater Blvd. North, Oakdale, MN (US) 55128

( * ) Notice: Subject to any disclaimer, the term of this patent is extended or adjusted under 35 U.S.C. 154(b) by 46 days.

(21) Appl. No.: 12/009,091

(22) Filed: Jan. 16, 2008

(65) Prior Publication Data
US 2009/0181462 A1 Jul. 16, 2009

(51) Int. Cl.
*C07C 327/00* (2006.01)
(52) U.S. Cl. .................. 562/26; 436/120
(58) Field of Classification Search ............ 562/26; 436/120
See application file for complete search history.

(56) References Cited

U.S. PATENT DOCUMENTS 6,278,015 B1 * 8/2001 Spangler et al. ............ 560/227

OTHER PUBLICATIONS

Smith et al. (March's Advanced Organic Chemistry: Reactions, Mechanisms and Structure, 2001, 5th Ed., John Wiley &Sons, NY, pp. 142-143).*
Gauthier et al. (J. Med Chem. (1990), 33 (10): 2841-2845).*
Nelson et al. (Organometallics (1992), 11 (6): 2181-2189).*
Cabri, W. et al. 1994. Zinc halide-mediated nucleophilic attack of thioacid salts in nonprotic media. A key step in the total synthesis of penems. Tetrahedron Letters 35:3379-82.
Crossland, RK et al. 1970. A facile synthesis of methanesulfonate esters. J. Org. Chem. 35:3195-3196.
Dale, J.A., et al. 1969. α-methoxy-α-trifluoromethylphenylacetic acid, a versatile reagent for determination of enantiomeric composition of alcohols and amines. J. Org. Chem. 34:2543-2549.
Ellingboe, E.K. 1963. Thiolacetic acid. Organic Synthesis CV4:928-931.
Givens, R.S. et al. 1984. Photoextrusion of $SO_2$ from arylmethyl sulfones: exploration of the mechanism by chemical trapping, chiral, and CIDNP probes. J. Am. Chem. Soc. 106:1779-1789.
Schmidt, S.P. et al. 1987. 1,2-bis (diphenylphosphineo)ethane tetrahalide: a convenient reagent for the conversion of alcohols to the corresponding halides. Tetrahedron Letters 28:767-768.
Shin, H.-C. et al. 1993. A simple and efficient synthesis of fatty thioacids. Lipids 28:73-74.
Stein, A.R. 1994. β-deuterium kinetic isotope effects for identity purposes: bormide ion substitution at 1-bromo-1-arylethanes and 2-bromooctane. Can. J. Chem. 72:1789-1796.
Strijtveen, B. et al. 1986. Synthesis of (racemization prone) optically active thiols by $S_N2$ substitution using cesium thiocarboxylates. J. Org. Chem. 51:3664-3671.
Volante, R.P. 1981. A new, highly efficient method for the conversion of alcohols to thioesters and thiols. Tetrahedron Letters 22:3119-3122.

* cited by examiner

*Primary Examiner*—Kamal A Saeed
*Assistant Examiner*—Valerie Rodriguez-Garcia
(74) *Attorney, Agent, or Firm*—Hugh McTavish

(57) ABSTRACT

The invention provides novel chiral compounds including 2-methoxy-2-trifluoromethylphenylacetic thioacid useful to react with and analyze other chiral compounds that have an electrophilic chiral carbon center.

11 Claims, 4 Drawing Sheets

Scheme 2

*Scheme 1*

(S)-8a, Ar = 2-Naphythl
(S)-8b, Ar = 2-Bromophenyl

11

12-HBr, X = Br
12-HI, X = I

THIOACIDS AND THIOACID SALTS FOR DETERMINING THE ENANTIOMERIC EXCESS OF CHIRAL COMPOUNDS CONTAINING AN ELECTROPHILIC CARBON CENTER

BACKGROUND

Since its introduction nearly forty years ago, Mosher's acid (2-methoxy-2-triflouromethylphenylacetic acid 1), (1) and the corresponding acid chloride (2) have found increasing use as agents for determining the enantiomeric excess of amines and alcohols by NMR and other methods (2).

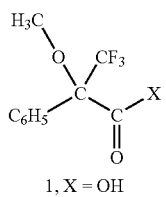

1, X = OH
2, X = Cl

Other reagents are needed that can be used to determine the stereochemistry of other chiral compounds, particularly those that do not react well with Mosher's acid.

SUMMARY

The invention involves a compound of formula I or a salt thereof:

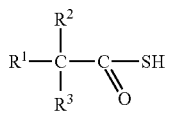

I wherein $R^1$, $R^2$, and $R^3$ are each independently ($C_1$-$C_6$) alkyl, ($C_3$-$C_6$)cycloalkyl, ($C_1$-$C_6$)alkoxy, aryl, aryloxy, aryl ($C_1$-$C_3$)alkyl, aryl($C_1$-$C_3$)alkoxy, wherein any cycloalkyl, alkyl, or aryl group is optionally substituted with one or more halo, oxo, hydroxy, methoxy, ethoxy, acetoxy, acetamido, cyano, nitro, nitroso, methylmercapto, ethylmercapto, carboxyl, sulfonate, or sulfinate groups; and wherein any cycloalkyl or aryl group is additionally optionally substituted with one or more methyl or ethyl; wherein none of $R^1$, $R^2$, and $R^3$ are identical to each other (that is, the compound is chiral). Preferably no two of $R^1$, $R^2$, and $R^3$ are linked together to form a cycloalkyl or aryl ring. Preferably, no $R^1$, $R^2$, or $R^3$ is of the formula $R^4$—C(=O)—O—, wherein $R^4$ is any atom or group.

The thioacid group of a compound of formula I is nucleophilic. Even more so the ionized thiocarboxylate group, which is the ionized form of a compound of formula I, is an excellent nucleophile that can react with many electrophilic carbon centers. A particular compound of formula I, 2-methoxy-2-triflouromethylphenylacetic thioacid, also referred to herein as Mosher's thioacid, is found by the inventor to be stable in air. The inventor has also found that it can be synthesized with retention of configuration and high chemical and optical purity.

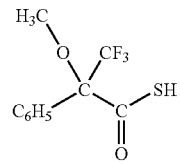

2-methoxy-2-trifluoromethylphenylacetic thioacid,
Mosher's thioacid

The salt of Mosher's thioacid with 1,8-bis(dimethylamino) naphthalene forms crystals that are soluble in organic solvents and remarkably stable in air.

Another embodiment of the invention provides a method of analyzing a test compound having an electrophilic carbon center, wherein the test compound is a compound of formula IIa or IIb,

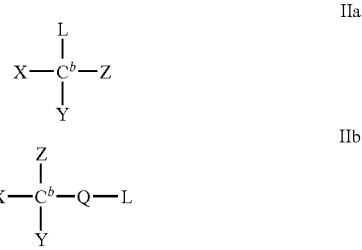

wherein X, Y, and Z are independently any atom or group, L is a leaving atom or group, Q is a group having an electrophilic carbon atom, none of L, X, Y, and Z is identical to each other and none of X, Y, Z, and Q-L is identical to each other;

the method comprising reacting the test compound with a compound of formula I or a salt thereof,

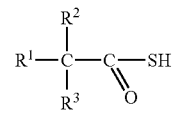

I wherein $R^1$, $R^2$, and $R^3$ are each independently ($C_1$-$C_6$) alkyl, ($C_3$-$C_6$)cycloalkyl, ($C_1$-$C_6$)alkoxy, aryl, aryloxy, aryl ($C_1$-$C_3$)alkyl, aryl($C_1$-$C_3$)alkoxy, wherein any cycloalkyl, alkyl, or aryl group is optionally substituted with one or more halo, oxo, hydroxy, methoxy, ethoxy, acetoxy, acetamido, cyano, nitro, nitroso, methylmercapto, ethylmercapto, carboxyl, sulfonate, or sulfinate groups; and wherein any cycloalkyl or aryl group is additionally optionally substituted with one or more methyl or ethyl; wherein none of $R^1$, $R^2$, and $R^3$ are identical to each other;

to form an adduct of formula IIIa or IIIb

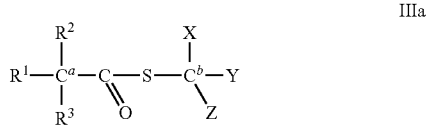

IIIa

-continued

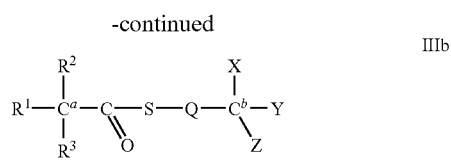

IIIb and analyzing the stereochemistry of the adduct to determine the stereochemistry of chiral center $C^a$ or $C^b$ in the adduct.

DETAILED DESCRIPTION

Figure 1:
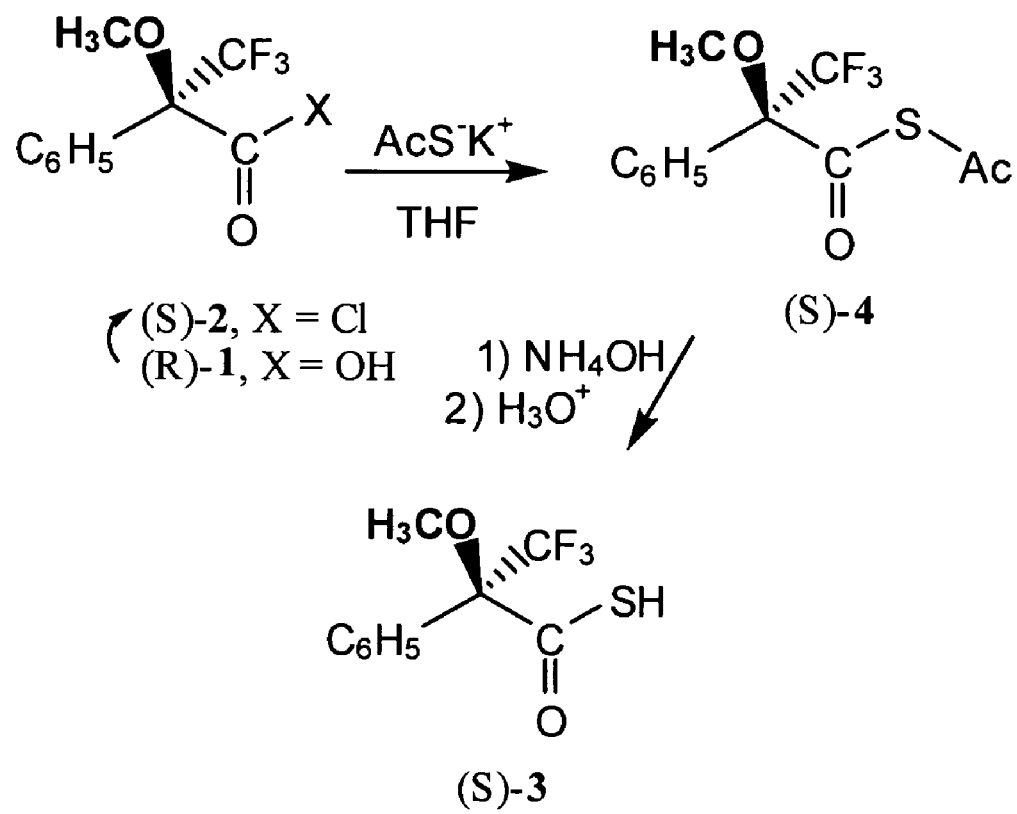
FIGS. 1-5 show reaction schemes used in the Example and the structures of compounds used or produced in the Example.

Definitions:

The term "aryl" as used herein refers to a 5-10-member conjugated ring system. It includes groups having only carbon atoms in the ring system and groups having hetero ring atoms. Preferred aryl groups in the compounds of formula I are phenyl and naphthyl.

The terms "alkyl" and "cycloalkyl" include groups having only saturated C—C bonds or one or more unsaturated C—C bonds.

Unless specifically stated that cycloalkyl, alkyl, or aryl are optionally substituted, they are not optionally substituted. Where it is stated that a cycloalkyl, alkyl or aryl group is optionally interrupted or substituted, this applies to the cyclo alkyl, alkyl, and aryl as components of larger groups as well, such as alkoxy, aryloxy, arylalkyl, etc.

Description:

One embodiment of the invention provides a compound of formula I or a salt thereof:

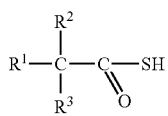

I wherein $R^1$, $R^2$, and $R^3$ are each independently $(C_1-C_6)$ alkyl, $(C_3-C_6)$cycloalkyl, $(C_1-C_6)$alkoxy, aryl, aryloxy, aryl $(C_1-C_3)$alkyl, aryl$(C_1-C_3)$alkoxy, wherein any cycloalkyl, alkyl, or aryl group is optionally substituted with one or more halo, oxo, hydroxy, methoxy, ethoxy, acetoxy, acetamido, cyano, nitro, nitroso, methylmercapto, ethylmercapto, carboxyl, sulfonate, or sulfinate groups; and wherein any cycloalkyl or aryl group is additionally optionally substituted with one or more methyl or ethyl; wherein none of $R^1$, $R^2$, and $R^3$ are identical to each other (that is, the compound is chiral). Preferably no two of $R^1$, $R^2$, and $R^3$ are linked together to form a cycloalkyl or aryl ring. Preferably, no $R^1$, $R^2$, or $R^3$ is of the formula $R^4$—C(=O)—O—, wherein $R^4$ is any atom or group.

In a particular embodiment, $R^1$ is $(C_1-C_6)$alkoxy, aryloxy, aryl$(C_1-C_3)$alkoxy; $R^2$ is $(C_1-C_6)$alkyl, $(C_3-C_6)$cycloalkyl, or aryl$(C_1-C_3)$alkyl; and $R^3$ is aryl; wherein any cycloalkyl, alkyl, or aryl group is optionally substituted with one or more halo, oxo, hydroxy, methoxy, ethoxy, acetoxy, acetamido, cyano, nitro, nitroso, methylmercapto, ethylmercapto, carboxyl, sulfonate, or sulfinate groups; and wherein any cycloalkyl or aryl group is additionally optionally substituted with one or more methyl or ethyl.

In a particular embodiment, $R^1$ is $(C_1-C_6)$alkoxy, wherein the alkyl group of alkoxy is optionally substituted with one or more halo; $R^2$ is $(C_1-C_6)$alkyl optionally substituted with one or more halo; and $R^3$ is aryl.

In a particular embodiment, $R^1$ is $(C_1-C_6)$alkoxy, $(C_1-C_6)$ alkyl, or benzyloxy, wherein the alkyl and phenyl groups are optionally substituted with one or more halo; $R^2$ is $(C_1-C_6)$ alkyl optionally substituted with one or more halo, and $R^3$ is aryl, aryl$(C_1-C_3)$alkyl, or benzyloxy.

In a particular embodiment $R^1$ methoxy, ethoxy, or benzyloxy; $R^2$ is methyl or ethyl, optionally substituted with one or more halo; and $R^3$ is phenyl or naphthyl.

In a specific embodiment, $R^1$ is methoxy, ethoxy, methyl, or ethyl; $R^2$ is methyl or ethyl, optionally substituted with one or more halo; and $R^3$ is phenyl or naphthyl.

In a specific embodiment, $R^1$ is methoxy, ethoxy, or benzyloxy; $R^2$ is $CF_3$; and $R^3$ is phenyl or naphthyl.

In a specific embodiment $R^1$ is methoxy, $R^2$ is $CF_3$, and $R^3$ is phenyl.

Another embodiment of the invention is a salt of the thiocarboxylate anion of the compound of formula I with a cation. In a particular embodiment, the cation is an alkali metal cation. In another particular embodiment, the cation is the protonated form of the nitrogen bases ammonia, amines, diamines and triamines. In another particular embodiment, the cation is the amidinium or a substituted amidinium ion or a guanidinium or substituted guanidinium ion. In another particular embodiment, the cation is a quaternary ammonium ion. In a specific embodiment, the salt is the thiocarboxylate anion of a compound of formula I complexed with the protonated form of the diamine, 1,8-bis(dimethylamino)naphthalene In one embodiment of the invention the composition comprises the compound of formula I or salt thereof in at least a 20:1 ratio of R:S or S:R stereoisomers.

Another embodiment of the invention provides a method of analyzing a test compound of formula IIa or IIb having an electrophilic carbon center, involving reacting the test compound with a compound of formula I or a salt thereof to form an adduct of formula IIIa or IIIb and analyzing the stereochemistry of the adduct to determine the stereochemistry of chiral center $C^a$ or $C^b$ in the adduct. In the compound of formula IIa, the electrophilic carbon center is the chiral carbon center $C^b$. But the chiral carbon $C^b$ may be a different carbon atom from the electrophilic carbon atom that bonds to the S of the compound of formula I. Where the chiral carbon $C^b$ is different from the electrophilic carbon, the method involves reacting a compound of formula IIb with a compound of formula I to form the adduct IIIb.

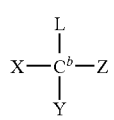

IIa

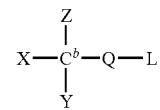

IIb

In the compound of formula IIa or IIb X, Y, and Z are independently any atom or group, L is a leaving atom or group, and Q is a group having an electrophilic carbon atom. Two or more of the groups on carbon $C^b$ can be linked to form one or more rings, provided $C^b$ is chiral.

An example of a compound of formula IIb that can be reacted with Mosher's thioacid salt to form an adduct of formula IIIb is compound 13 below.

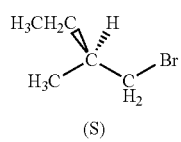

13

(S)

Typically, in the method of analyzing a test compound, the compound of formula I or salt thereof is a pure enantiomer, that is, at least 95% one enantiomer or the other, or a highly pure enantiomer that is at least 99% one enantiomer or the other. In other embodiments, it is at least two-thirds one enantiomer or the other. In some embodiments, the compound of formula I or salt thereof is a racemic mixture, with equal amounts of both R and S stereoisomers. In that case, part of the analysis may be to determine which enantiomer preferentially reacts with which enantiomer of the compound of formula II.

In the method of analyzing a test compound, the adduct of formula III may be analyzed by various techniques including NMR spectroscopy, polarimetry, gas chromatography (GC), mass spectrometry (MS), infrared spectroscopy, coupled GC/MS, liquid chromatography, HPLC, and HPLC/MS.

One embodiment of the method of analyzing a test compound comprises determining enantiomeric excess of the test compound of formula II by determining the diastereomeric excess of the test compound of the adduct of formula III. The enantiomeric excess (ee) is the excess percent or fraction of a compound that is one enantiomer. For instance, if 90% of a mixture is the R enantiomer and 10% is the S enantiomer, the mixture has an 80% enantiomeric excess of the R enantiomer (90%-10%) compared to the racemic content (10% R+10% S). The diastereomeric excess is the analagous term for diastereomers.

In the example below, the method is used to analyze the stereochemistry and reactivity of α-bromobenzylic compounds, benzylic methanesulfonate (mesylate) esters, and benzylic alcohols. Thus, in some embodiments, the leaving group L in the compound of formula II is halo or methanesulfonate or even hydroxyl groups (activated under Mitsunobu conditions). In more specific embodiments, it is bromo, chloro, or iodo. In other embodiments, the leaving group L is a diazonium ($RN_2^+ 13 > N_2$), pseudohalide (e.g., benzotriazole or thiocyanate), sulfonium ($R_3S^+ \to R_2S$) or oxonium ($R_3O^+ \to R_2O$) group.

One embodiment of the method of analyzing a test compound involves determining whether the test compound reacts with the compound of formula I stereospecifically by $S_N2$ mechanism (3). This can be determined by whether the stereochemistry of $C^b$ chiral center in the adduct of formula IIIa is cleanly inverted from the stereochemistry of the $C^b$ chiral center in the test compound of formula IIa.

The invention will now be illustrated by the following example, which is intended to illustrate the invention but not limit its scope.

EXAMPLE

We have found that Mosher's thioacid (3, shown below) is readily prepared and easily forms stable salts with organic bases. It is shown in this example that these salts are very powerful nucleophiles useful for detecting the enantiomeric excess (ee) of optically active benzylic bromides.

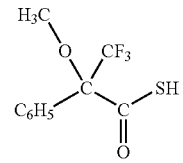

2-methoxy-2-trifluoromethylphenylacetic thioacid, Mosher's thioacid

Mosher's thioacid, 3, can be prepared by treating the acid chloride 2 with hydrogen sulfide. Although this route is economical, attaining high conversions requires careful control of highly toxic and corrosive gases under pressure (4). As such, this approach is not convenient for a laboratory synthesis.

Shin and Quinn (5) describe the preparation of fatty thioacids from fatty acid chlorides using thioacetic acid as a convenient and inexpensive carrier of hydrogen sulfide. This method gives a practical laboratory synthesis of Mosher's thioacid, which easily operates even on very small scale. Workup using an excess of aqueous ammonia (6) and then acid, produces optically active Mosher's thioacid with retention of configuration and high chemical and optical purity. This is shown in Scheme 1 (FIG. 1).

The nucleophilicities of thioacids ($pK_a \approx 3.5$) are activated by conversion to their salts, thiocarboxylate ions. We have found that either the racemic or resolved salts of Mosher's thioacid (5) neutralized with slightly less than one equivalent of PROTON SPONGE [1,8-bis(dimethylamino)naphthalene] are readily recrystallized from minimal ethanol producing colorless shiny non-hygroscopic crystals that are remarkably stable in air and soluble in chloroform-d and many other organic solvents (7).

To check the reactivity of 5, two optically active benzylic bromides, 7a and 7b, were prepared using the especially mild method of Schmidt and Brooks (8a) and described by Stein (8b).

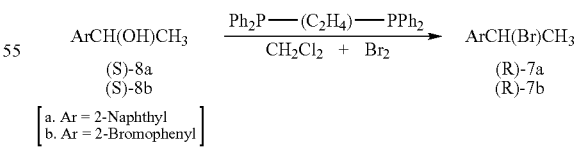

Figure 2:
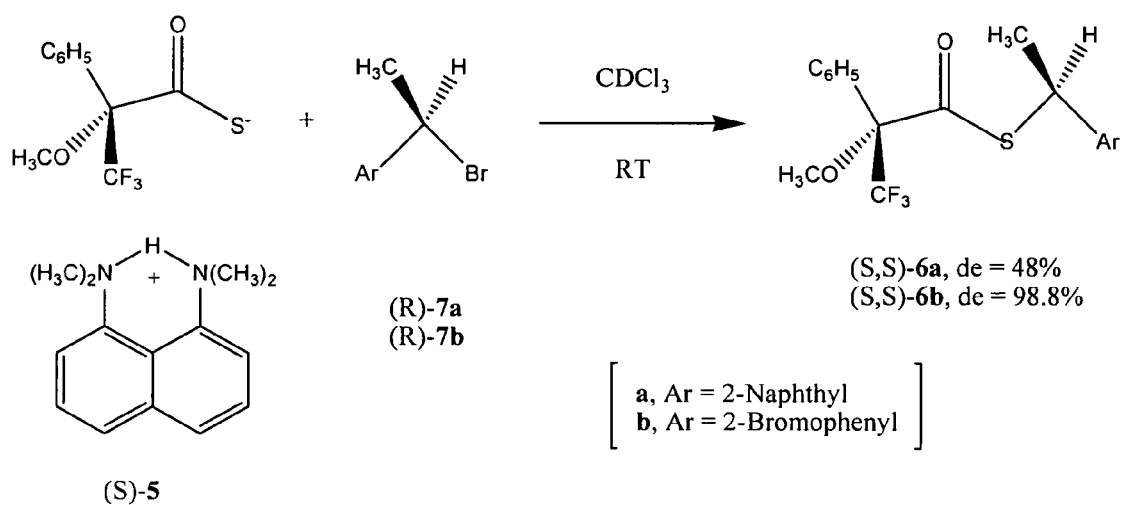

We found that the nucleophilicity of 5 is sufficient even in $CDCl_3$ for dilute solutions to react cleanly with these benzylic bromides at room temperature to produce (predominantly $S_N2$ inverted) benzylic thiolesters, 6 (Scheme 2, FIG. 2). Elimination side reactions are insignificant and racemization is minimal, especially in the early stages of these reactions (9).

Considering this, reagent 5 is excellent for determining the enantiomer excess (ee) of benzylic bromides, 7 (10). For this purpose, NMR integrations of the methoxy quartet (11), or the trifluoromethyl singlet (11) of Mosher's acyl groups, or the methyl doublet of the phenethyl groups can be used to determine the diastereomeric excess (de) of the predominant (S,S)-diastereomers (10c), 6, produced from (R)-7. Chromatographic analyses provide a more sensitive determination of diastereomer ratios, which is especially useful in the early stages of these reactions, when racemization of 7 is negligible.

Both benzylic bromides 7a and 7b were prepared from the corresponding (S)-alcohols of high optical purity. Both preparations used conditions essentially identical to those described by Stein (8). Our results (de values in Scheme 2), show two very different ee values for the similar bromides 7a and 7b. At least in our hands, the stereochemical integrity of Stein's method can differ markedly even in these two closely related cases. This difference is readily detected by reagent (S)-5.

Figure 3:
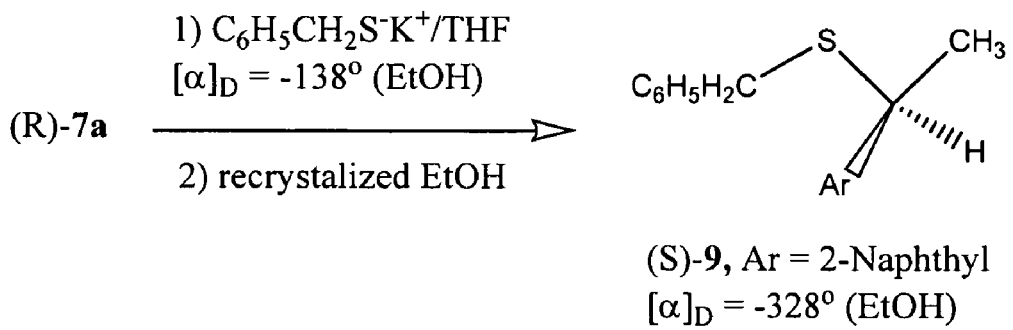

In order to unambiguously establish the ee of 7a, a second determination was undertaken. Givens, et al. (12) previously reported the optically active (S)-chloro analogue of 7a and prepared the (R)-benzyl thioether, 9, from it ($[\alpha]_D$=+92.6°, EtOH). The optical purities of neither of these compounds were determined. We repeated this reaction with bromide (R)-7a and obtained a somewhat greater absolute value for the rotation of 9, ($[\alpha]_D$=−138°, EtOH) (FIG. 3). In our hands, this thioether crystallized and on recrystallization from ethanol, the observed rotation reached a constant value 2.36 times the initial value ($[\alpha]_D$=−328°, 0.5% in EtOH) (13). This is consistent with the initial optical purity of 9 being ≧42%, in reasonable agreement with the value of 48% seen for the de of derivative 6a produced from 7a (14).

The low ee of (R)-7a was further confirmed by our finding that (R)-7a ($[\alpha]_D$≈+23°) (15) can be recrystallized from pentane to a much higher optical purity: $[\alpha]_D^{26}$=+64.3° (1%, pentane) (13). Reaction of these crystals with (S)-5 (see experimental) indicates that they have reached 94% ee. The optical activity of crude (R)-7a indicates that the ee is ≧43%.

Figure 4:
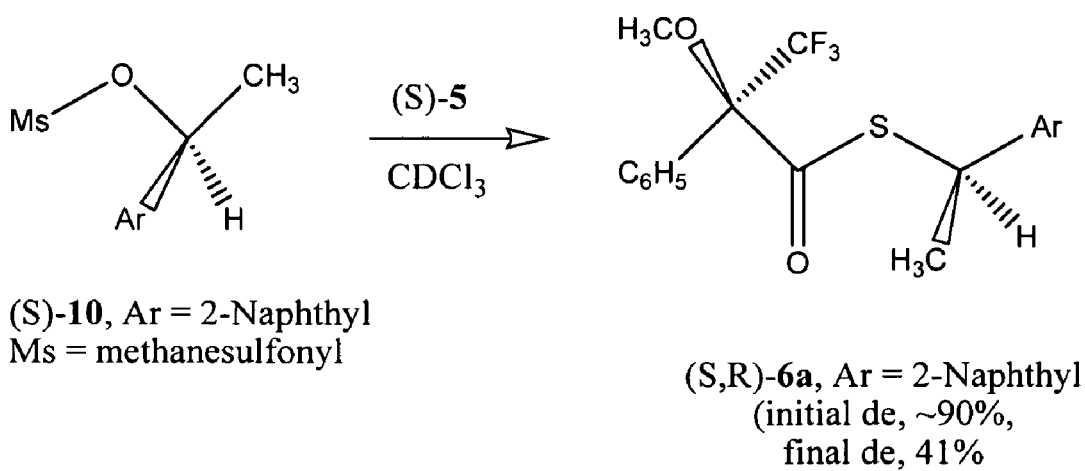
Figure 5:
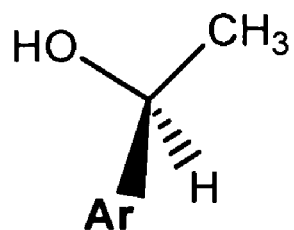
Figure 5:
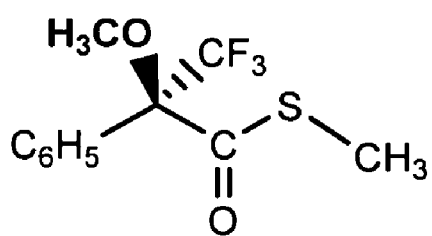
Figure 5:
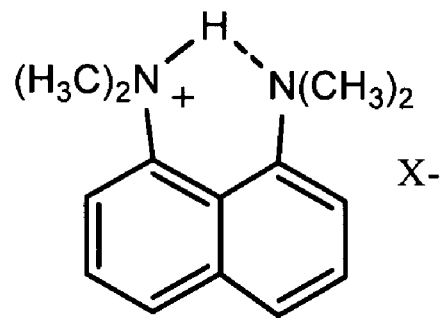

To explore the utility of reagent (S)-5 for determining the ee of more active benzylic methanesulfonate esters, we prepared mesylate 10 from (S)-8a by reaction of (S)-8a in methanesulfonyl chloride/$Et_3N$ (16). Following the reaction of 10 with reagent (S)-5 (FIG. 4), by NMR we observed that the de of the major product, the expected (S,R)-diastereomer of 6a in this case, decreased significantly as the reaction proceeded. This suggests that racemization is more significant in this case than in the reaction of (S)-5 with (R)-7a. Extrapolating the de values back to the initial time (t=0) indicates that the initial ee of 10 was quite high (85-95%).

This was confirmed again by applying Given's method (12). The thioether derivative of 10 was prepared and the optical activity of the product, (R)-9, indicates that the ee of 10 was ≧83%. This value must be considered to represent a lower limit for the ee, because racemization of 10 probably compromised this result, too. Less than quantitative yields of the $S_N2$ products [75% for 6a and 90% for (R)-9] further limit the application of both of these approaches for determining the ee of very active mesylate esters.

Finally, we have demonstrated the activation of alcohol (S)-8a for direct reaction with Mosher's thioacid, (S)-3, in $CDCl_3$ under Mitsunobu conditions (17). As is expected, the (S,R)-diastereomer of thioester 6a, the product of a single inversion, greatly predominates. Analyses by $^{19}F$ NMR show that the de is >85% at completion (94% by GC/MS). Unfortunately, racemization and side reactions again compete with the desired $S_N2$ reaction.

We conclude that the optically active Mosher's (S)-thioacid, (S)-3, and its salt (S)-5 are highly effective agents for determining the ee of benzylic bromides and other less reactive alkyl halides, reacting with clean $S_N2$ inversion. They are also highly reactive agents for determining the ee of other similarly reactive electrophilic compounds. For even more reactive electrophilic compounds, competing reactions can compromise the results and may require extra care to properly evaluate.

Supplemental Information

I. Experimental

A. General

Infrared spectra were recorded on Midac Corp. "M Series" FT-IR either as KBr pellets or between salts (NaCl). NMR spectra were recorded on Varian VXR or VI Spectrometers at 300 ($^1H$), 282 ($^{19}F$) or 75.5 MHz ($^{13}C$) in $CDCl_3$ with respectively internal TMS, F-11 and $CDCl_3$ (assigned as 77.23 ppm) references. Abbreviations: s, singlet; d, doublet; t, triplet; q, quartet; m, multiplet; b, broad; st, strong; w, weak; v, very and sh, shoulder. Proton spectra were acquired with four transients and 20 second pulse delay. Integrated fluorine spectra were acquired with 4000 Hz sweep width, sixteen transients, two second acquisition time and three second pulse delay. Carbon spectra are broad-band proton-decoupled. Mass spectra were recorded at low resolution as direct electrospray injections (5 μL loop) on a Thermo Fisher LCQ Classic Ion Trap instrument in positive and negative ion modes. GC/MS data were collected on a Hewlett Packard 5973 quadrupole sector MS and HP 6890 GC with 30 m bonded 5% phenyl/dimethylsilicone (5% phenyl) or 100% dimethylsilicone (100% methyl) capillary columns and He carrier gas (1 mL/min): the temperature program started at 100° C. and increased at 10° C./min to 300° C. Polarimetry was done on a Jasco DIP-370 Digital Polarimeter with 3 mm aperture in 5 cm path-length, (1.42 mL) cell at 589 nm. Routinely, five readings each with 20 second integration time were averaged. UV/visible spectra were acquired on a Beckman DU 7400 diode array spectrophotometer with 1 cm quartz cells. HPLC was done on a Zorbax 300 SB-C18 reversed phase column (an Absorbosphere C18 5μcolumn failed) with 100% acetonitrile (AN) to 75% AN-25% isopropanol linear gradient over 30 min, flow rate 1 mL/min. Elemental analyses (by combustion) were done by Galbraith Labs, Inc., Knoxville, Tenn. Chemicals were purchased from Sigma-Aldrich Company.

B. Mosher's (S)-Thioacid, (S)-3, from Mosher's (R)-Acid, (R)-1.

Note that the preparation and spectral properties of the racemic thioacid from racemic acid are identical to this procedure. Also, note that Mosher's (S)-acid chloride, (S)-2, is commercially available. A two-neck 15-mL flask with stopcock/$N_2$ inlet, stir bar and condenser fitted with $N_2$ sweep across the top was charged with 204 mg of moist (hygroscopic) (R)-(+)-Mosher's acid, (R)-1, (<0.87 mmol), 2 μL of DMF (catalyst) and a large excess (0.5-1 mL) of thionyl chloride. This mixture was refluxed for 2 h. The condenser was exchanged for a sublimer head with a Dry-Ice condenser sufficiently enclosed so that, for transfer, the cold finger could later be flushed with $N_2$, avoiding exposure to air. Thionyl chloride was briefly refluxed off the cold finger. The entire apparatus was brought to 30-40° C. and swept with $N_2$ to remove $SOCl_2$ (to base trap). The cold finger was chilled to 0° C. and the sublimer was evacuated to 1 Torr (mm of Hg) to remove the last trace of $SOCl_2$. The cold finger was cooled to <−100° C. with ethanol slush (liq. $N_2$) and the pressure was lowered to 0.02 Torr. The acid chloride, (S)-2, sublimed under these conditions. Note that at −78° C., this acid chloride can remain liquid and is sufficiently fluid to reflux off the cold finger.

A similar dry two-neck ice-cooled reaction flask with stir bar and stopcock/$N_2$ inlet was charged under $N_2$ with 5 mL of anhydrous THF, 2.0 mL of 1M KOtBu/THF (2 mmol) and 205 μL (excess) of thioacetic acid forming a translucent slurry of potassium thioacetate. Under positive flows of $N_2$, the cold finger with the sublimed acid chloride (S)-2 was transferred to the flask containing the ice-cooled thioacetate slurry. Condensing THF and a final rinse with 2 mL additional THF washed the acid chloride off the cold finger (−78° C.) into the reaction flask, which was then stirred at RT for 30 min. This reaction mixture was mixed briefly with 10 mL of cold 15% aqueous ammonia and the resulting yellow solution was acidified quickly (6N HCl) and the thioacid extracted into three washes of dichlormethane. (Extraction of the basic mixture with $CH_2Cl_2$ before acidification is necessary to remove impurities if the reaction has discolored to amber or red. This also helps to remove THF (+$H_2O$), which is responsible for extracting the ammonium salt of 3 from the acidified mixture.) Concentration left 267 mg of wet (water+THF) yellow thioacid, (S)-3. Distillation by vacuum transfer (60-70° C./0.02 Torr) to a cold receiver gave 199 mg (~90% yield) of yellow (S)-3 contaminated with colorless crystals of the ammonium salt of 3. Analytical data and subsequent reactions were done on the yellow thioacid phase, which is soluble in pentane (recovered by concentrating) and readily separated from the insoluble crystals.

Polarimetry: $[\alpha]_D^{26}$=+86±1° (1.1% in EtOH).

IR, neat, between salts, closely resembles Mosher's acid chloride (exceptions underlined): 3065 (vw), 2989 (w), 2951 (w), 2849 (w), 2562 (b w, SH), 2361 (w, overtone), ca. 1706 (v b, st, C=O), 1496 (w), 1451 (w), 1264 (st), 1223 (m), 1172 (b, st), 1132 (m), 1094 (w), 1079 (w), 1035 (vw), 999 (m), 937 (m), 908 (m), 810 (m), 798 (m), 761 (m), 726 (m), 716 (st), 698 (m), 683 (w) and 668 $cm^{-1}$ (vw).

$^1$H NMR: 3.63 (q, C$\underline{H}_3$O, $^5J_{HF}$=1.8 Hz), 4.78 (b s, S$\underline{H}$, sometimes v b), 7.56 (m, 2H, ortho), 7.40-7.47 ppm (m, 3H, meta and para).

$^{19}$F NMR: −69.02 ppm (s, $CF_3$, proton coupling not resolved). Only trace impurities are seen in the $^1$H and $^{19}$F NMR spectra.

$^{13}$C NMR on (RS)-3: 196.06 ($\underline{C}$=O), 130.17 (Ar, st), 128.89 (Ar, st), 127.46 (Ar, b, st, q, J~1 Hz), 131.78 (C-1 aryl), 123.04 (q, $\underline{C}F_3$, $^1J_{CF}$=291 Hz), 87.81 (q, $^2J_{CF}$=26 Hz), 55.94 ppm (q, $\underline{C}H_3O$, $^4J_{CF}$ ca. 2 Hz, partially resolved).

GC/MS (5% phenyl): 6-7 min (broad trailing peak), m/e 189 ($C_9H_8F_3O^+$, 100%), no molecular ion.

UV ($CH_3CN$): generally decreasing absorbance from 210 to 350 nm with shoulders near 217 (ε=7.0×$10^3$), 234 (3.6× $10^3$) and weak $\lambda_{max}$ at 262 (6.7×$10^2$) and 268 nm (5.7×$10^2$). Note, however, that dilutions do not appear to strictly follow Beer's Law. For example, three values for $\epsilon_{290}$ are 178 (9.2 mM), 197 (1.84 mM) and 262 (0.184 mM), consistent with more ionization at higher dilution. Furthermore, the $\epsilon_{290}$ decreased when this solution was acidified (HCl) and increased dramatically when a small amount of aqueous tetrabutylammonium hydroxide was added.

Alternative workup for the racemic thioacid from the racemic acid chloride without ammonia quench, but distillation instead, produced (RS)-3 contaminated with mixed diacyl sulfide (RS)-4: $^{19}$F NMR, −69.34 ppm (s); $^1$H NMR, 3.635 (q, C$\underline{H}_3$O) and 2.55 ppm (s, C$\underline{H}_3$CO) and IR, 1767 $cm^{-1}$ (C=O). Also produced by this workup, but not fully characterized, are two pairs of meso/d,l-diastereomers, presumably the diacyl sulfides and diacyl disulfides of Mosher's acyl group. These two pairs of diastereomers show nearly equal intensity signals at −69.47 and −69.51 ($^{19}$F) and 3.48 and 3.60 ppm (q, C$\underline{H}_3$O) and the other at −69.69 and −69.71 ($^{19}$F) and 3.64 and 3.65 ppm (q). These five impurities were not detected in the thioacid product from workup by washing with aqueous ammonia.

C. Salts of Mosher's Thioacid with PROTON SPONGE: (RS)-5 and (S)-5.

The crystalline salts of either Mosher's (RS)- or (S)-thioacids with 1,8-bis(dimethylamino)naphthalene (PROTON SPONGE) readily form upon mixing the thioacids and the base. To maintain neutrality, a slight excess of the thioacid was used. Racemic and resolved salts usually pack in different crystal lattices. (This is true except in relatively rare cases where racemic compounds crystallize as conglomerate mixtures of the two enantiomeric crystals. See reference 2, page 7.) That a racemate is not a conglomerate of (R)— and (S)-enantiomers is shown by observing different properties and spectra in the solid states of the (R)— or (S)— and (RS)-compounds. (See reference 2, pp 18-19.) Both the racemic and optically active salts (RS)-5 and (S)-5 recrystallize from minimal (1-3 parts of) absolute ethanol but grow in distinctly different habits: the racemic crystals appear to be nearly spherical (octahedral ?) and the (S)-crystals are distinctly elongated, clear, nearly colorless prisms. Both forms exposed to air melt over a broad range and, surprisingly, both melt sharply at very similar temperatures with decomposition (off-gasing) when they are sealed under vacuum: racemic mp 137.0-137.8° and (S)-5 mp 138.5-139° after a single recrystallization from ethanol.

Polarimetry on (S)-5: $[\alpha]_D^{27.5}$=+69.3±1° (1%, EtOH).

IR: in the solid state the IR spectra of these crystals as KBr pellets show little resemblance to Mosher's thioacid (liquid film between salts) and also are quite different from each other. (RS)-5: 3300-3700 (v b w, NH), 2800-3100 (CH, especially prominent 2941 and 2998 and lesser sharp bands at 2817, 2841 and 3067), 1559 (b st, $COS^-$), ~1460 (b m), 1410 (sharp, w), 1255 (st), 1222 (m), 1169 (st), 1195 (m), 1152 (st), 1138 (st), 1083 (m), 999 (m), 927 (sharp, w), 847 (st), 829 (m), 767 (st) and 721 $cm^{-1}$ (st). (S)-5: 3300-3700 (v b w, NH), 2800-3100 (CH, especially prominent 2998 and several lesser bands), 1555 (b st, $COS^-$), 1465 (b w), 1254 (m), 1165 (st), 1159 (st), 1135 (st), 1125 (sh m), 1111 (m), 1082 (w), 1033 (m), 1001 (m), 845 (st), 833 (m), 771 (st), 764 (m), 722 (st) and 655 $cm^{-1}$ (b w).

$^1$H NMR: 7.89 (b d, 2H), 7.78 (b d, 2H), 7.68 (v b s, 2H), 7.62 (t, 2H), 7.22-7.34 (m, 3H), 3.81 (q, C$\underline{H}_3$O, $^5J_{HF}$=1.6 Hz), 3.22 (b s, 12H, C$\underline{H}_3$N) and 1.5-1.9 ppm (v b s, N$\underline{H}$).

$^{19}$F NMR: −67.92 ppm (b s, $CF_3$).

$^{13}$C NMR: 209.47 ($\underline{C}OS^-$), 125.30 (q, $\underline{C}F_3$, $^1J_{CF}$=292 Hz), 89.15 (quat. C, $^2J_{CF}$=22 Hz), 54.95 (q, $\underline{C}H_3O$, $^4J_{CF}$~5 Hz, not fully resolved), 46.87 (st, $\underline{C}H_3N$) and ten distinct aryl carbons at 145.03 (w), 137.71 (w), 135.65 (w), 129.16 (b m), 127.91 (st), 127.72 (st), 127.59 (st), 127.14 (st), 121.22 (b, s) and 119.07 ppm (w).

MS (MeOH): Positive ion mode, 215.25 (Calc'd for $C_{14}H_{19}N_2^+$, 215.15, 100%) and 200 (10%). Negative ion mode, 248.87 (Calc'd for $C_{10}H_8F_3O_2S^-$, 249.02), 188.9 ($C_9H_8F_3O^-$, 70%), 155.1 (15%), 265.1 (12), 113.0 (11) and 61.9 (14).

Anal. Calc'd (Found) for $C_{24}H_{27}F_3N_2O_2S$: C, 62.05 (61.91); H, 5.86 (5.86); N, 6.03 (5.98); S, 6.90 (7.13) %.

UV ($CH_3CN$): $\lambda_{max}$ 274 ($\epsilon$=10.2±0.3×10$^3$ and $\lambda_{max}$ 222 nm ($\epsilon$=6.1×10$^4$).

D. Use of Salt (S)-5 for Determining the Lower Limit for the ee of (R)-1-Bromo-1-(2-naphthyl)ethane, (R)-7a: Single-Reaction Method 1.

A 5 mm NMR tube was charged with 4.7 mg (0.010 mmol) of crystals of salt (S)-5. This readily dissolved in CDCl$_3$ to 5 cm depth. NMR spectra ($^1$H and $^{19}$F) showed 5 with a low level (7 mole %) of ethanol impurity. This was mixed with 2 mg of crystals of (R)-7a ($[\alpha]_D$≈+23°). Note that excess 5 is necessary to assure complete reaction of 7a, thus avoiding kinetic sorting at the end. NMR ($^1$H and $^{19}$F) of this solution showed 5 and 7a in 1:0.82 mole ratio. After 30 min. at 20° C., the spectra showed 30% conversion of 7a cleanly to (S,S) and (S,R) diastereomers in ~2.5:1 ratio. At 18 h, NMR showed 97% conversion to 3:1 mixture of the diastereomers (de≈50%). No more 7a was detected after an additional 24 h at 25° C. The final integration ratio of the two singlets at −69.42 and −69.28 ppm in the $^{19}$F NMR spectrum was 2.8 (de≧47%)* for the major (S,S)-6a and minor (S,R)-6a diastereomers. Proton NMR assignments for these are, respectively: 3.54 and 3.49 (q, C$\underline{H}_3$O, $^5J_{HF}$=1.7 Hz), 1.76 and 1.71 (d, C$\underline{H}_3$CH, $^3J_{HH}$=7 Hz), 4.89 and 4.91 (overlapping q, CH$_3$C$\underline{H}$) and 7.18-7.95 ppm (m, 12 aryl H, not resolved). Note that large crystals of the HBr salt of PROTON SPONGE (12-HBr) separated in the course of this reaction but did not interfere with NMR acquisitions and integrations.

HPLC purification (Zorbax C18 column) of a sample of the final NMR solution showed that the ionic products eluted quickly and the diastereomers of 6a eluted together (and were collected) at 10-11 min. GC/MS on this eluate (100% methyl column) cleanly resolved the two diastereomers eluting at 17.19 and 17.63 min, integrating in the ratio 100:34.7, respectively (de=48%). (Minor racemization of 7a which occurs predominantly near the end of this single-reaction method, sets a lower limit to the value of ee that is determined from these de values by this method.) The ei mass spectra are virtually identical: m/e 404 ($C_{22}H_{19}F_3O_2S$, M$^+$, 2%), 189 ($C_9H_8F_3O^+$, 9%) and 155 ($C_{12}H_{11}^+$, 100%).

E. Use of Salt (S)-5 for Determining the ee of Purified (R)-1-Bromo-1-(2-naphthyl)ethane, (R)-7a, the Extent of Racemization and the Relative Enantiomer Reaction Rates in the Formation of Diastereomers 6a: Full Double-Reaction Method.

Rationale.

Rigorous definition of the ee of benzylic bromides by determining the diastereomeric product ratio formed in their reaction with (S)-5 requires the determination of the degree (if any) of racemization that accompanies these reactions. Racemization of the benzylic bromide primarily occurs by $S_N2$ reaction (inversion) with the liberated ionic bromide. Initially, the ionic bromide concentration, [Br$^-$], (and racemization by this mechanism) is zero. The rate of racemization increases as the reaction proceeds and [Br$^-$] increases. Evaluating the de for the reaction of (S)-5 with (R)-7a at low conversion and extrapolating to t=0 eliminates the complication of racemization occurring by this competing $S_N2$ reaction. However, sampling at low conversions introduces other considerations. First, early sampling requires a means for quenching the reaction. Second, the de of the desired $S_N2$ reaction is affected not only by the relative concentrations of the (R)— and (S)-benzylic bromides, but also by their (unequal) reaction rates with (S)-5. Furthermore, if the much more sensitive technique of GC analysis (GC/MS or FID-GC, for example) is used rather than, or in addition to, NMR analyses, the relative GC detector sensitivities for the two diastereomers must be determined. And, of course, care must be taken to operate the detector in the range of linear response.

Two closely related and straightforward experiments address these considerations: first, the reaction of racemic (RS)-benzylic bromide with an excess of (S)-5 is sampled and quenched at early and late reaction time points and the de values are determined at each extreme and, second, the reaction of excess (S)-5 is repeated with racemic benzylic bromide. Integrals for the equimolar diasteromeric products from the first reaction [(RS)-bromide] determined at completion of the reaction indicate the relative detector sensitivities for the two diasteromers. Early time points in this same series (corrected for any difference in the detector sensitivities) plotted back to t=0, indicate the ratio of the two $S_N2$ reaction rate constants for the reactions of the (R)— and (S)-bromides with (S)-5. Factoring these two results into the results of the second experiment (with optically active bromide) gives the corrected initial diastereomer ratio (and de values) from the early reaction data (projected to the initial time, t=0). The difference between the early de values and the corrected de values from later time points indicate the extent of racemization that has occurred subsequently. The following experiment demonstrates this method.

Quenching.

First, to check the suitability of methyl iodide for quenching these reactions [forming the methyl thioester (11) of Mosher's thioacid], an NMR experiment roughly followed the rate of this reaction. Initially, 50 μL of a solution of 4 μL of CH$_3$I in 0.5 mL of CDCl$_3$ was added to 2.85 mg (6.1 μmol) of (S)-5 in 0.7 mL of CDCl$_3$ (+Fll and TMS). The first $^1$H and $^{19}$F NMR acquisitions at ~6 and ~10 min after mixing (19° C.) show that nearly equimolar amounts of (S)-5 and CH$_3$I were initially charged and that this reaction was already about 50% complete at 6 min and 65% complete at 10 min. After 1.5 h, this reaction was complete [no (S)-5, but a low level of (S)-3 (from HI?) was detected by $^{19}$F NMR] and the HI salt (12-HI) of PROTON SPONGE, 3 and 11 were the only products seen by NMR. This study indicates that the rate constant for the reaction of CH$_3$I with (S)-5 is at least ten times the rate constant for (S)-5 plus 7a. Subsequent use of CH$_3$I to quench reactions of (S)-5 plus 7a used at least a 10-fold excess of methyl iodide. The rate of the quenching reaction is ≧100 times the rate of the reaction being monitored under these conditions.

$^1$H NMR of 11: 7.52-7.57 (m, Ar$\underline{H}$, 2H), 7.39-7.44 (m, Ar$\underline{H}$, 3H), 3.57 (q, $^5J_{HF}$=1.7 Hz, C$\underline{H}_3$O) and 2.31 ppm (s, C$\underline{H}_3$S).

$^{19}$F NMR of 11: −69.40 ppm.

$^1$H NMR of 12-HI: 7.6-8.0 (m, Ar$\underline{H}$, 6H), 3.4 (bs, CH$_3$, 12H) and 1.6 ppm (s, NH).

Racemic Reaction.

For the reaction of (RS)-bromide with (S)-5, a 2 mL GC vial with Teflon-lined cap was charged with 1.27 mg (5.4 μmol) of (RS)-7a crystals and 2.85 mg (6.1 μmol) of (S)-5 crystals (kept apart). This reaction was initiated by adding 0.80 mL of CDCl$_3$ and shaking. Samples of 200 μL each were quenched at 5, 20 and 80 min. The remaining reaction mixture was allowed to continue for 2800 min total when it was diluted for $^1$H and $^{19}$F NMR without addition of methyl iodide—the methyl thioester (11) interferes with the integrations of the diastereomer $CF_3$ singlets. These NMR spectra show that excess (S)-5, but no 7a, remains in the late sample. Integrations of the $^{19}F$ NMR signals of (S,R)-6a and (S,S)-6a indicate that the two diastereomers were present in the ratio 1.027:1; i.e., 1:1 (as is expected) within the accuracy limits of NMR integrations. For GC/MS analyses, all four samples were filtered through 0.5 g of silica gel/dichloromethane to remove the salts. The filtrates (1 µL), with appropriate dilutions, were injected on the 100% methyl GC column and detected and integrated using the MS detector with the highly sensitive mass selection for the m/e 155 base peak. At the completion of this reaction, peaks at 17.0 and 17.5 minutes [(S,S)-6a and (S,R)-6a diastereomers, respectively] were detected in the ratio 1:0.984 (±0.002). This indicates that these two diastereomers show essentially identical sensitivities in this selective ion detection mode. Repeated integrations by this method for the chromatograms of the three earlier samples in this series, showed considerable scatter and no significant trend for the different early sample times. From these three times, the average for the ratios of the peaks for these diastereomers was 1:0.94 (±0.02), indicating that the second order rate constant for the formation of the (S,S)-diastereomer is only 95% (94/0.984) of the rate constant for formation of the (S,R)-diastereomer.

Chiral Reaction.

This experiment was repeated for the reaction of (S)-5 with optically purified (see Section M) (R)-7a ($[\alpha]_D^{30}$=+64.3°) taking eight samples at 5, 10, 20, 40, 80, 160, 320 and 1110 min. The initial charges were 1.2 mg of (R)-7a (5.1 µmol) and 3 mg of (S)-5 (6-7 µmol). The quenched, silica-filtered samples were analyzed as above. Although there is considerable scatter in the results, there is a definite trend toward an increasing level of the minor (S,R)-diastereomer from the early to the later samples. For the early (5, 10 and 20 min), medium (40, 80, 160 and 320 min) and late (1110 min) time points, the level increased from 3.2±0.3% to 3.9±0.7% and finally to 4.5% at the final time, when the reaction was about 90% complete. [This data includes the correction factors of 0.94 (GC-MS) and 0.95 (NMR) determined in the preceding paragraph.] Another similar experiment (with close to equimolar reactants) allowed to go essentially to completion and analyzed by both NMR and GC/MS methods shows the minor diastereomer [(S,R)-6a] had increased to 6.4% over the course of that entire reaction, which corresponds to a de of 88% for the major (S,S)-diastereomer. It is clear that the final stages of this reaction are accompanied by extensive racemization of the minor amount of (R)-7a that remains at the end. This is reasonable since the rate of the second-order reaction of (S)-5 with the benzylic bromide is decreasing much more rapidly than the rate of the pseudo-first-order reaction of the benzylic bromide with ionic bromide. The concentration of bromide ion remains almost constant and quite high near the end of the reaction. [This assumes that the hydrogen bromide salt of PROTON SPONGE (12-HBr) has not precipitated in the course of this reaction. Precipitation often does occur near the end. Even then, after the salt precipitates, the concentration of dissolved bromide remains higher than the concentration of (S)-5.]

The level of 3.2% determined for the minor (S,R)-diastereomer at the first time points (5-20 min) is essentially the t=0 intercept. This corresponds to the initial de for the (S,S)-diastereomer and the ee for the starting (R)-7a being 94%. When (S)-5 was charged in only minor excess, by the end of the reaction, an overall additional 8% racemization of 7a has occurred, mostly in the final phase of the reaction.

F. Use of Salt (S)-5 for Determining the Lower Limit for the ee of (R)-1-Bromo-1-(2-bromophenyl)-ethane, (R)-7b: Single-Reaction Method 1.

This experiment was done similarly to the single-reaction method used for (R)-7a with nearly equimolar charges of the reactants. The charge was 6.7 mg (14 µmol) of (S)-5 crystals and 3.5 mg (13 µmol) of (R)-7b ($[\alpha]_D$≈−47.8°, see Section O), 1:0.92 mole ratio. Early NMR spectra detected the (S,S)-diastereomer of the thioester product (−69.49 ppm by $^{19}F$ NMR) with no indication of the (S,R)-diastereomer. (See Section G, however.) After 18 h the reaction was 85-90% complete and the de for the (S,S)-diasteromer was 97%. After six days, bromide 7b was no longer detected by NMR. As above (Section D), large crystals of the HBr salt of PROTON SPONGE (12-HBr) separated in the course of this reaction, but did not interfere with NMR acquisitions and integrations. The ratio of (S,S)— and (S,R)-diastereomers seen at −69.49 and −69.30 ppm in the final spectrum was 1:0.020 (de=96%). This corresponds to an initial ee for the starting (R)-7b being ≧96%. (Once again, minor racemization of 7b, which occurs predominantly near the end of this single-reaction method, sets the lower limit for the value of ee that is determined.) (See Section G.) Proton assignments for the (S,S)— and (S,R)-diastereomers are: 3.54 and 3.57 (q, C$\underline{H}_3$O, $^5J_{HF}$=1.7 Hz), 1.68 and 1.62 (d, C$\underline{H}_3$CH, $^3J_{HH}$=7 Hz), 5.10 and 5.11 (overlapping q, CH$_3$C$\underline{H}$) and 7.06-7.56 ppm (m, 9 aryl H, not resolved). Assignments for the lesser diastereomer were made by comparison with spectra of that same product prepared from (RS)-7b.

HPLC purification was essentially identical to that described above for reaction of (R)-7a. Subsequently, GC/MS (100% methyl column) cleanly resolved the major (S,S)— and minor (S,R)-diastereomers eluting at 14.92 and 15.11 min in the ratio 100:3.4 (de=93.4%). Again, the ei mass spectra of the two diastereomers are essentially identical. Neither show a molecular ion. The base peak is m/e 189 ($C_9H_8F_3O^+$, 100%). Bromine containing ions are seen at m/e 183/185 ($C_8H_8Br^+$, 30% for each, 60% total), 199/201. ($C_8H_8BrO^+$, 1% total), 215/217 ($C_8H_8BrS^+$, 0.6% total) and 214/216 ($C_8H_7BrS^+$, 0.5% total). Other ions (without bromine) are m/e 77, 91, 103, 104, 105, 119 and 135.

G. Use of Salt (S)-5 in Large Excess Over (R)-7b to Limit Racemization: Preferred Single-Reaction Method 2 and Short Double Reaction Method.

Rationale.

A second way to limit racemization during the completion phase of the reaction of (S)-5 with benzylic bromide (R)-7b is to maintain a substantial excess of (S)-5. If ≧100% excess of (S)-5 is present initially, then the concentration of Mosher's thiocarboxylate will exceed the concentration of ionic bromide throughout the reaction. Since Mosher's thiocarboxylate clearly reacts faster than ionic bromide with benzylic bromides, the desired thioester formation will greatly prevail. Near the completion of the reaction, although racemization will not have been completely eliminated, its effect will be much smaller than in the case where the reactants are nearly equimolar.

Demonstration.

A 0.75-mL GC vial was charged with 1.8 mg (6.8 µmol) of benzylic bromide (R)-7b ($[\alpha]_D$=−47.8°, see Section O) and 0.1 mL of CDCl$_3$. Then 7.5 mg (16.1 µmol) of(S)-5 crystals and 0.3 mL of CDCl$_3$ was mixed into this solution. After 2 min reaction at 25° C., half of this reaction mixture was quenched with CH$_3$I/CDCl$_3$. Crystals (the HI salt of PROTON SPONGE, 12-HI) separated almost immediately. This sample was filtered through silica gel and eluted with dichloromethane. Analysis of the filtrate by GC/MS shows an intense peak for the methyl thioester 11 at 6.4 min and a low level (~10%) of the (S,S)-diastereomer of 6b at 14.68 min. Only a very weak peak (<1% relative to the major diastereomers) eluted at 14.90 min for the minor diastereomer, (S,R)-6b. The more sensitive selective ion chromatogram for the base peak at m/e 189 and the weaker pair of ions at m/e 183 and 185 gave good integrations for this weak peak as being 0.76±0.1% of the (S,S) peak. Assuming that the detector sensitivities and the formation rate constants for the two diastereomers are not greatly different (checked below), from these results one can conclude that the ee of the starting benzylic bromide, (R)-7b, is very high (≧98%, probably 98.5±0.2%).

After 24 h, the remaining reaction mixture was diluted with $CDCl_3$ for NMR analysis. The $^1H$ spectrum no longer detects 7b. Integrations of the $^{19}F$ NMR spectrum of this mixture show the minor diastereomer, (S,R)-6b, represents only 1-2% of the major diastereomer (de is 96-98%) at the end of the reaction. More accurate GC/MS data show 1.1±0.2% for (S,R)-diastereomer for de 97.8±0.4%. In this case, racemization during the course of the reaction was less important than was observed in Section F.

Integration Bias.

A single experiment with quenching of the early reaction of (RS)-5 plus (R)-7b or (RS)-7b plus (S)-5, determines the kinetic-sensitivity factor [for the combined effects of different detector sensitivities and kinetics of formation for the two diastereomers (S,S) and (R, S) in the first case or, equally, (S,S) and (S,R) in the example that follows].

In a GC vial, 3.6 mg (7.7 μmol) of (S)-5 was dissolved in 0.1 mL of $CDCl_3$. Then 0.94 mg (3.6 μmol) of (R,S)-7b was washed in with 0.1 mL of $CDCl_3$. Two min after mixing, the reaction was quenched by adding excess $CH_3I/CDCl_3$, filtered through 0.5 g of silica with dichloromethane and analyzed by GC/MS as above. The ratio of the peaks for (S,S)— and (S,R)-diastereomers was 0.80 (±0.02):1 from the average of nine integral ratios from m/e 189, 183 and 185 selective ion chromatograms and three injections. This corrects the value of the de for 6b and the ee for 7b (98.5% above) to 98.8±0.2%.

H. Use of Salt (S)-5 for Determining the ee of (S)-Methanesulfonate Ester (10) of (S)-1-(2-naphthyl)ethanol, (S)-8a.

Mesylate ester 10 was prepared from (S)-8a by a modification of the procedure of Crossland and Servis.[16] The reaction was done in THF (not dichloromethane) to enhance the solubility of the alcohol. To a solution of 218 mg (1.24 mmol) of 98% (S)-8a in 5 mL of anhydrous THF stirred at 0° C., was added 250 μL (1.8 mmol) of triethylamine and then, dropwise, 158 mg (~110 μL, 1.38 mmol, 11% excess) of methanesulfonyl chloride. This was stirred ½ h at 0° C., then 5 mL of pentane were added. This cold slurry was diluted to 25.0 mL with 1:1 THF-pentane and allowed to settle. Then 0.2 mL of the supernate was transferred and concentrated cold ($N_2$ then vacuum to 0.1 Torr). The colorless residue was dissolved in $CDCl_3$ (+TMS+F-11) and transferred to a cold NMR tube containing 4.6 mg (10 μmol) of (S)-5 crystals. This was maintained cold (0° C.) for 2 h then warmed to 20° C. for NMR acquisitions, which show a small excess of 5 and 24% conversion of 10 (by integrations of $ROSO_2CH_3$ and $CH_3SO_3^-$ at 2.70 and 2.82 ppm). The thioester products, for which the (S,R)-diastereomer of 6 predominates, have formed with de=0.78, but only in ~75% yield at that time. Acquisition after 1 h at 35° C. shows 58% conversion and de=0.56. Final acquisitions after 18 h at 25° C. show a 99% conversion of 10 mainly to the diastereomeric thioesters (de=0.41) in ~70% yield. Major side products are 2-vinylnaphthalene and alcohol 8a.

These results are consistent with racemization competing with the desired $S_N2$ reactions. Extrapolating the de values back to 0% conversion suggests that the initial de value is approximately 0.85-0.95. Note, however, that this determination was not corrected for enantiomer kinetic selection in the calculated value of de. No attempt was made to evaluate the kinetic factor.

I. (S)-Methanesulfonate Ester (10) of (S)-1-(2-Naphthyl) ethanol, (S)-8a, and Determination of the Optical Purity of the Predominantly (R)-Enantiomer of Benzyl 1-(2-Naphthyl) ethyl Sulfide, (R)-9.

The preparation of 10 was done essentially as described above (Section H). The slurry resulting after the first 5 mL of pentane had been added was filtered cold and the $Et_3N.HCl$ solids were washed with minimal cold 1:1 pentane/THF. The combined filtrates were maintained cold and concentrated to 3 g of solution of 10.

$^1H$ NMR: 7.91 (d, 1H), 7.84-7.88 (m, 3H), 7.52-7.56 (m, 3H), 5.90 (q, C$\underline{H}$CH$_3$), 2.70 (s, 3H, C$\underline{H}_3$SO$_2$) and 1.82 ppm (d, CHC$\underline{H}_3$, J=7 Hz).

In a second side-arm flask, to a slurry of 38 mg of NaH (1.6 mmol, pentane-washed/$N_2$-dried mineral oil dispersion) in 6 mL of anhydrous THF, was added 194 mg (1.56 mmol) of benzyl mercaptan. A thick suspension resulted. This readily dissolved by adding 0.6 mL of absolute ethanol. Approximately 85% of this solution (1.3 mmol) was added with stirring to the crude mesylate ester (cold, THF solution from above). The thick slurry that resulted was allowed to warm to 25° C. and stir for 30 min, then it was poured into 25 mL of dichloromethane plus 25 mL of water and swirled. The organic phase was combined with a second wash of the aqueous layer, dried ($Na_2SO_4$) and concentrated under vacuum to 359 mg of oily residue. Overnight at +5° C., this oil crystallized. The $^1H$ NMR showed that this product is 85-90% (by wt.) pure thioester 9, ~90% yield. Polarimetry gave $[\alpha]_D^{25}$=+ 239° (1% in EtOH). Corrected for purity, the $[\alpha]_D^{25}$=+ 273±10°. A single recrystallization of this crude product from ethanol gave optically pure crystals, $[\alpha]_D^{25}$=+329° (1% in EtOH) and show that the optical purity of the initial product is 83±3%.

J. Determination of the ee of Optically Active (R)-1-Bromo-1-(2-naphthyl)ethane, (R)-7a, by Formation of the Benzyl (S)-1-(2-Naphthyl)ethyl Sulfide Derivative, (S)-9.

To an ice-cold slurry of 497 mg (2.1 mmol) of the optically active crystals of (R)-7a ($[\alpha]_D$≈+23°, see Section M) in 7 mL of absolute ethanol stirred under nitrogen, was added 7 mL of sodium benzylthiolate in ethanol (prepared from 266 mg, 2.14 mmol, of benzyl mercaptan and 49 mg of sodium metal, 2.1 mg atom, in 7 mL ethanol). The resulting solution was warmed briefly nearly to reflux, then was cooled to 25° C. The pH of this solution was weakly basic (~8) and required 0.05 mmol of acid (HCl) to neutralize it. The neutral solution was concentrated and the residue was slurried in 1:1 pentane/ dichloromethane and filtered to remove salts. The residue, after concentrating (596 mg), crystallized at +5° C. overnight. Analysis by NMR shows that this residue is 96% (by wt.) pure 7a (~97% yield, 0.6% by wt. benzyl mercaptan, 1.5% dibenzyl disulfide and 1.9% 2-vinylnaphthylene). Polarimetry showed $[\alpha]_D^{25}$=−132° (1% in EtOH), which corrected for purity gives $[\alpha]_D^{25}$=−138°. Two recrystallizations from ethanol increased (the absolute value of) the rotation to $[\alpha]_D^{25}$=− 328°, which did not change on further recrystallization. The optical activity of the initial (S)-9, and presumably also the ee of (R)-7a, is 42%. [The lower value of ee here compared to the de of Mosher's thioester, 6a (47%, see Section D) may reflect slight racemization induced by the more basic sodium benzyl thiolate nucleophile.] The mp of optically pure (S)-9 is 61.5-63.5° C. (from EtOH).

IR (KBr): 2850-3100 [CH, similar, but not identical to (RS)-9 melt spectrum between salts], 1597 (m), 1506 (w), 1494 (m), 1452 (m), 1400-1000 [similar, but not identical to (RS)-9 melt], 964 (m), 862 (m), 821 (st), 750 (st) and 701 cm$^{-1}$, (st).

$^1$H NMR: 7.78-7.87 (m, 3H, naph), 7.66 (s, 1H, naph C-1), 7.55 (dd, J=8.5, 1.6 Hz, 1H, naph), 7.43-7.73 (m, 2H, naph), 7.18-7.32 (m, 5H, phenyl), 3.98 (q, C$\underline{H}$CH$_3$), 3.53 and 3.42 (AB, prochiral C$\underline{H}_2$), J=13.5 Hz) and 1.61 ppm (d, CHC$\underline{H}_3$, J=7 Hz), essentially as reported by Givens, et al. (12).

GC/MS (eluting at 17.3 min, 273° C., on 5% phenyl column): m/e 278 (M$^+$, 20%), 155 (C$_{12}$H$_{11}^+$, 100%) and other-predominant ions at 91, 115, 127, 128, 152, 153, 154 and 156.

K. Benzyl (RS)-1-(2-Naphthyl)ethyl Sulfide, (RS)-9: A Racemic Conglomerate

To an ice-cold solution of 1.08 g (6.17 mmol) of 98% (RS)-1-(2-naphthyl)ethanol, (RS)-8a, and 0.85 g (8.5 mmol) of triethylamine in 25 mL of anhydrous THF, 0.83 g (7.2 mmol) of methanesulfonyl chloride was added dropwise with stirring. This slurry (Et$_3$N.HCl) was stirred ½ h at 0° C.

In a second flask, to a slurry of 161 mg (6.7 mmol) of pentane-washed mineral-oil dispersion (N$_2$ dried) sodium hydride in 10 mL of anhydrous THF was added 820 mg (6.6 mmol) of benzyl mercaptan and 0.5 mL of absolute ethanol to dissolve the sodium benzyl thiolate.

The cold methanesulfonate/THF slurry (above) was diluted with 25 mL of pentane and filtered cold. The filtrate and washes were concentrated to 15 mL and the solution of sodium benzyl thiolate was added slowly. The resulting slurry of sodium methanesulfonate was stirred 20 min at 25° C., then poured into water and extracted into dichloromethane. The combined organic phases were washed with water, dried (Na$_2$SO$_4$), concentrated and evacuated at 80° C./0.02 Torr leaving 1.80 g of residual oil. Theoretical yield is 1.75 g. When this was cooled (+5° C.) and seeded with (R)- and (S)-9, this mix slowly solidified, mp 34-49° C. NMR indicated that it was only 90% pure 9. Attempts to purify this product by recrystallization failed. Distillation of 100 mg in a micro-sublimer removed volatiles (dibenzyl disulfide) boiling to 95° C./0.01 Torr. The distillate collected boiling to 113° C./0.01 Torr (bath temperature) crystallized on cooling (+5° C.) overnight, mp 30.5-31.5° C. The $^1$H NMR spectrum (CDCl$_3$) is identical to that of the (S)-enantiomer (Section J).

The IR spectrum of the (RS)-product as a KBr pellet is identical to the IR of (RS)-9 as a melt between salts. Apparently, the process of cold grinding and pressing (+5° C.) induced melting in the KBr pellet:

IR (KBr): C—H at 3084 (w), 3056 (m), 3027 (m), 2967 (m), 2923 (m) and 2866 (w), 1600 (m), 1507 (w), 1495 (m), 1433 (m), 1315, 1270, 1125, 1071, 1047, 1029, 1019, 948, 892 (all are w), 857 (m), 818 (st), 749 (st) and 701 (st). Note: significant discrepancies in the C—H stretch values from those reported by Givens et al.$^{12}$ probably reflect the difference between prism and diffraction grating dispersion instruments. When the melt between salts of (RS)-9 was allowed to solidify, the IR spectrum changed and became essentially identical to the KBr spectrum of (S)-9, reported above (Section J). This finding indicates that (RS)-9 is an example of the somewhat rare class of racemates referred to as conglomerate racemates (see reference 2, pp 18-19), where the racemate does not have a unique crystal lattice.

L. Reaction of (S)-1-(2-Naphthyl)ethanol Directly with Mosher's (S)-Thioacid under Mitsunobu Conditions An NMR tube was charged with 2.4 mg (0.010 mmol) of Mosher's (S)-thioacid, (S)-3, and 1.4 mg (0.009 mmol) of (S)-1-(2-naphthyl)ethanol and CDCl$_3$ to 5 cm depth. NMR shows that the thioacid is in slight excess. Then 5.2 mg (0.020 mmol) of triphenylphosphine were added. The NMR of the thioacid did not change—no salt formed. Finally, 4.3 µL of 94% diisopropyl azodicarboxylate (~0.020 mmol) were added at 20° C. After 22 h at 25° C., the $^{19}$F NMR spectrum shows the (S,R)-diastereomer of thioester 6a at −69.29 ppm in large excess (de>85%) over a weak peak at −69.42 ppm for (S,S)-6a. Other $^{19}$F signals, especially −67.99 for the salt of Mosher's thioacid, indicate that the yield of thioesters 6a is only 50-70%. Side products and co-products were not identified in the $^1$H NMR spectrum, which is complex.

HPLC purification of this crude product mixture, followed by GC/MS analysis (100% methyl) shows de for (S,R)-6a is 94%. No attempt was made to study the degree of racemization at early time points.

M. (R)-1-Bromo-1-(2-naphthyl)ethane, (R)-7a, from (S)-1-(2-Naphthyl)ethanol [(S)-8a], Diphos and Bromine An ice-cold anhydrous solution of 599 mg (3.75 mmol) of bromine in 2 mL of dry dichloromethane was added slowly to a cold (0° C.) anhydrous solution of 762 mg (1.9 mmol) of 1,2-bis(diphenylphosphino)ethane (diphos) in 7 mL of dry dichloromethane. This solution was stirred 5 min at 0° C. and developed a white precipitate of the adduct in a light amber solution. Then a solution of 532 mg (3.1 mmol) of (S)-7a in 2 mL of dry dichloromethane was added in portions. A new precipitate (diphosdioxide dihydrobromide) separated. This slurry was warmed slowly to 25° C. and stirred for 15 min. Then 30 mL of dry ether and 60 mL of pentane were added. After 15 min this slurry was filtered through a coarse glass frit into a dry glass vessel for cold storage (−15° C.) under nitrogen. The original optical activity of this solution ($\alpha_D^{25}$=+0.080°, 0.6 wt % in the mixed solvents in 5 cm cell) was stable for several months. NMR shows that a concentrated sample of this crude product is >90% pure 7a (3 wt % 2-vinylnaphthylene and ca. 3-5% other aryl impurities, probably related to diphos): [α]$_D$≈+23°. Otherwise, the spectral properties of this product are identical to those of (RS)-7a reported by Bull, et al. (18). Concentration of the crude product produced off-white crystals which sublime at 50° C./0.4 Torr as colorless crystals, mp 71-76° C.

A second similar preparation of (R)-7a produced the chiral bromide in considerably higher optical purity ([α]$_D^{26}$=+37°), about 60% higher than the first preparation. Concentration of this solution and recrystallization from pentane increased the optical activity to +49°. Another sample, recrystallized four times, showed irregular increases in the optical activity to a high value: [α]$_D^{30}$=+64.3°, 1% in pentane, mp=78-84° C. (See Section E for determination of 94% as the ee of this sample.)

IR (KBr): 3057, 2991, 2969, 2923 (all w), 2860 (vw), 1598 (w), 1507 (w), 1437 (w), 1378 (m), 1364 (w), 1302 (w), 953 (vw), 903 (w), 899 (w), 866 (m), 824 (st), 752 (st), 704 (w), 661 (m), and 622 cm$^{-1}$ (w).

N. (RS)-1-Bromo-1-(2-naphthyl)ethane, (RS)-7a: A Racemic Conglomerate

A sample of the racemic bromide (RS)-7a, prepared similarly and recrystallized from pentane melts at 61-63.5° C. [lit. 63-64 (ref. 19) and 48-52 (ref. 20), both from petroleum ether]. The IR spectrum of these crystals (KBr pellet) is identical to the IR spectrum of the (R)-enantiomer (ee=94%) described above (Section M). As is discussed above for (RS)-9 (Section K), this observation indicates that (RS)-7a also exists as a racemic conglomerate.

UV (2-propanol): $\lambda_{max}$ 229, ($\epsilon$=5±0.5×10$^4$), 268, (6.5±0.6×10$^3$) and 277 nm, (6.9±0.6×10$^3$).

O. (R)- and (RS)-1-Bromo-1-(2-bromophenyl)ethane, 7b, from 1-(2-Bromophenyl)ethanol (8b)

The preparation of (R)-7b from (S)-8b, diphos and bromine was done essentially as for the 2-naphthyl analogue, (S)-8a, using a 20% excess of the diphosibromine reagent. Charges were 594 mg of diphos (1.5 mmol), 475 mg of bromine 3.0 mmol) and 6 mL of dichloromethane. The adduct did not precipitate this time. Next, 497 mg (2.47 mmol) of (S)-8b in 3 mL of dichloromethane, then 21 mL of ether and 42 mL of pentane were added. Filtration produced a clear, nearly-colorless (faintly amber) solution stored at −15° C. ($\alpha_D^{25}$=−0.297° in 5 cm cell). The optical activity appears to be stable for several weeks. NMR indicates that this product is quite pure 7b with no contamination seen from o-bromostyrene or alcohol 8b. This product, (R)-7b, is liquid to below 0° C. However, cooling a pentane solution to −60° C. produced crystals of (R)-7b that survived as the solvent was pumped off under vacuum at −50° C.: mp −15 to −11° C.

Polarimetry: $[\alpha]_D^{29}$=−47.8±0.5° (1.8% in pentane).

IR (neat, between salts): 3850-3100 (C—H), 1471 (st), 1438 (st), 1377 (m), 1275 (m), 1210 (m), 1179 (m), 1059 (d, m), 1025 (st), 972 (m), 784 (m), 756 (st), 720 (st), and 662 cm$^{-1}$ (m).

UV (pentane): Nearly featureless declining absorbance from 210 to 300 nm with slight inflections (shoulders) near 276 and 283 nm; $\epsilon_{230}$=5.8×10$^3$, $\epsilon_{276}$=4.3×10$^2$, $\epsilon_{280}$~3×10$^2$, $^1$H NMR: 7.66 (dd, J=7.9 and 1.6 Hz), 7.55 (dd, 8.0, 1.2), 7.35 (td, 7.6, 1.2) and 7.15 (td, 7.7, 1.7)—all ArH, 1H each −5.61 (q, C$\underline{H}$CH$_3$, 6.9 ) and 2.04 ppm (d, CHC$\underline{H}_3$, 6.9).

The racemic form, (RS)-7b, was prepared from the reaction of 50% excess PBr$_3$ with (RS)-8b (21) in dichloromethane. The crude product was washed with water, dried (Na$_2$SO$_4$), concentrated and distilled bulb-to-bulb (50-60° C./0.02 Torr, lit (22) bp 85° C./2 Torr). NMR shows this product, (RS)-7b, 84% yield, is nearly as pure as (R)-7b, but, unlike the diphos product, is contaminated with 2% (by wt.) of o-bromostyrene.

GC/MS (100% methyl): 5.99 min; m/e 262/264/266 (M$^+$, C$_8$H$_8$Br$_2^+$, 3%), 247/249/251 (M-15$^+$, 1%, 183/185 (M-Br$^+$, 100%), 104 (38%), 103 (23), 77 (20) and 51 (12).

P. Attempts to Determine the ee of (R)-7a Using Mosher's Acid Sodium Salt in DMF/DMSO-d$_6$ Shaw and co-workers (23) have demonstrated clean ester formation from the alkylation of carboxylic acid sodium salts in HMPA and other dipolar aprotic solvents. We attempted to use that chemistry to determine the ee of (R)-7a. Mosher's (R)-acid (6.3 mg, 0.027 mmol ) was neutralized (pH 7.5) with aq. sodium hydroxide and dried to 6.9 mg, the theoretical weight for the anhydrous salt. This salt was dissolved in 0.55 mL of DMF (not deuterated) and 0.20 mL of DMSO-d$_6$ plus F-11, for internal reference. The $^{19}$F NMR spectrum showed the Mosher's acid sodium salt singlet at −69.15 ppm. This solution was mixed with 6.0 mg of (R)-7a (0.255 mmol, $[\alpha]_D$≈+23°, see Section M). After 1.5 h at 37° C., a single new $^{19}$F signal at −71.00 ppm indicated that the conversion to ester was about 60% complete. After two days at 37° C., $^{19}$F NMR shows two poorly resolved singlets at −70.91 and −70.94 ppm in the ratio ca. 70:30. If these two peaks represented the (R,S) and the (R,R)-diastereomeric esters, then this would correspond to ee=40% for (R)-7a. Further results suggest that this interpretation is not valid.

This NMR solution was concentrated (0.02 Torr) to 19 mg of moist residue, which was slurried in acetonitrile-d$_3$. NMR on this supernate shows two singlets for CF$_3$ in the ratio 36:64 at −71.33 and −71.31 ppm. The $^1$H NMR spectrum indicates, however, that there are three Mosher's acid related products. There are three quartets for C$\underline{H}_3$O in the ratio 45:18:36. Apparently, the $^{19}$F peak at −71.31 ppm represents the superposition of two CF$_3$ singlets (45+18). The product at the level of 18% is almost certainly Mosher's acid (from the salt plus HBr generated from dehydrobromination of 7a). If this is the case, then the ratio of the two diastereomeric esters is 45:36 (de=11%).

This result was supported by GC/MS analysis of the crude product mixture. GC/MS shows about a 60:40 mixture (de ~20%) of the diastereomeric esters eluting as poorly separated peaks at 16.97 and 17.01 min (5% phenyl column). The ei mass spectra of the two diasteromers are essentially identical: m/e 388 (M$^+$ for C$_{22}$H$_{19}$F$_3$O$_3$, 6%), 189 (6%), 158 (9), 157 (10), 127(7), 105 (4) and 77 (4).

The low value of ee (~15%) for (R)-7a determined in this experiment indicates that racemization of 7a is occurring in the process of ester formation. Apparently, sodium bromide, the co-product of this process, induces racemization (by S$_N$2 inversion of 7a) under these reaction conditions.

NOTES AND CITED REFERENCES (1) Dale, J. A.; Dull, D. L; Mosher, H. S. *J. Org. Chem.* 1969, 34, 2543-2549.
(2) Jacques, J.; Collet, A.; Wilen, S. H. *Enantiomers, Racemates, and Resolutions;* John Wiley & Sons: New York, N.Y., 1981, p. 335.
(3) Thiocarboxylate ions are less well known in this respect. For examples of these nucleophiles in S$_N$1 chemistry, see: Cabri, W.; Candiani, I.; Zarini, F.; Bedeschi, A. *Tetrahedron Lett.* 1994, 35, 3379-3382.
(4) For examples of thioacids prepared from hydrogen sulfide and acid chlorides see: a) Ellingboe, E. K. *Org. Syn.,* 1963, CV4, 928-931 and references therein, b) Loeliger, P.; Flükiger, E. *Org. Syn,* 1988, CV6, 776-780- see note 14 on p. 779.
(5) Shin, H.-C.; Quinn, D. M. *Lipids* 1993, 28, 73-74.
(6) Strijtveen, B.; Kellogg, R. M. J. Org. Chem. 1986, 52, 3664-3671.
(7) a) Elemental analyses (C, H, N, S) were acceptable (±0.3%) after a single recrystallization. b) Salt 5 reacts slowly with dichloromethane.
(8) a) Schmidt, S. P.; Brooks, D. E. *Tetrahedron Lett.* 1987, 767-768. b) Stein, A. R. *Can. J. Chem.* 1994, 72, 1789-1796.
(9) a) A comparison with similar reactions for the Na$^+$ salt of Mosher's acid is given in the Supplemental Information. b) Methodologies described in the Supplemental Information minimize and compensate for the effects of racemization in these reactions.
(10) a) The ee of enantiomer R (over S), defined as (R−S)/(R+S), is directly related to optical purity. The value of de for diastereomers is similarly defined. b) Assigning the ee value for the nucleofuge (7) as being equivalent to the de values of substitution products (6) rests on the assumptions that the ee of the nucleophile is high (>>99%) and the stereointegrity of the reactants, the SN reactions and the products are high. c) The configuration of the a-carbon of Mosher's acyl group is listed first followed by the configuration of the benzylic thiol carbon.
(11) The $^5J_{HF}$ of about 1.7 Hz is resolved in the $^1$H, but not the $^{19}$F NMR spectra of 6 that we acquired.

(12) Givens, R. S.; Hrinczenko, B.; Liu, J. H.-S.; Metuszewski; Tholen-Collison, J. *J. Am. Chem. Soc.* 1984, 106. 1779-1789.
(13) Observations reported in the Supporting Information indicate that both (RS)-7a and 9 exist as racemic conglomerates. See reference 2, p. 7.
(14) Errors for $[\alpha]_D$ values are estimated to be ±2%, for de values determined by NMR integrations, about ±3%, and by gc/ms, ≦2%.
(15) Accuracy for $[\alpha]_D$ is limited by unknown purity for crude 7a.
(16) Crossland, R. K.; Servis, K. L. *J. Org. Chem.* 1970, 35, 3195: modified procedure in THF.
(17) See, for a closely related example: Volente, R. P. *Tetrahedron Lett.* 1981, 22, 3119-3122.
(18) (Bull, S. D.; Davies, S. G.; Epstein, S. W.; Garner, A. C.; Mujtaba, N.; Roberts, P. M.; Savory, E. D.; Smith, A. D. *Tetrahedron*, 2006, 62, 7911-7925.)
(19) Bacon, R. G. R.; Guy, R. G.; Irvin, R. S. *J. Chem Soc.* 1961, 2436-2447.
(20) Klemm, I. H.; Solomon, W. C.; Kohlik, A. *J. J. Org Chem.* 1963, 27, 2777-2786.
(21) Marvel, C. S.; Moon, N. S. *J. Am. Chem. Soc.* 1940, 62, 45-49.
(22) Halpern, V.; Meidar, D. *Org. Prep. Procedures Int.* 1976, 8, 299-302.
(23) Shaw, J. E.; Kunerth, D. C.; Sherry, J. S.; *Tetrahedron Lett.* 1973, 689-692.

All patents, patent documents, and other references cited are incorporated by reference.

What is claimed is:

1. A composition comprising a compound of formula I or a salt thereof,

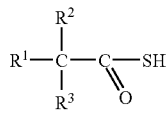

I wherein $R^1$, $R^2$, and $R^3$ are each independently $(C_1-C_6)$ alkyl, $(C_3-C_6)$cycloalkyl, $(C_1-C_6)$alkoxy, aryl, aryloxy, aryl$(C_1-C_3)$alkyl, aryl$(C_1-C_3)$alkoxy, wherein any cycloalkyl, alkyl, or aryl group is optionally substituted with one or more halo, oxo, hydroxy, methoxy, ethoxy, acetoxy, acetamido, cyano, nitro, nitroso, methylmercapto, ethylmercapto, carboxyl, sulfonate, or sulfinate groups; and wherein any cycloalkyl or aryl group is additionally optionally substituted with one or more methyl or ethyl; wherein none of $R^1$, $R^2$, and $R^3$ are identical to each other, and no two of $R^1$, $R^2$, and $R^3$ are linked together to form a cycloalkyl or aryl ring.

2. The composition of claim 1 wherein $R^1$ is $(C_1-C_6)$ alkoxy, aryloxy, aryl$(C_1-C_3)$alkoxy; $R^2$ is $(C_1-C_6)$alkyl, $(C_3-C_6)$cycloalkyl, or aryl$(C_1-C_3)$alkyl; and $R^3$ is aryl; wherein any cycloalkyl, alkyl, or aryl group is optionally substituted with one or more halo, oxo, hydroxy, methoxy, ethoxy, acetoxy, acetamido, cyano, nitro, nitroso, methylmercapto, ethylmercapto, carboxyl, sulfonate, or sulfinate groups; and wherein any cycloalkyl or aryl group is additionally optionally substituted with one or more methyl or ethyl.

3. The composition of claim 1 wherein $R^1$ is $(C_1-C_6)$ alkoxy, wherein the alkyl group of alkoxy is optionally substituted with one or more halo; $R^2$ is $(C_1-C_6)$alkyl optionally substituted with one or more halo; and $R^3$ is aryl.

4. The composition of claim 1 wherein $R^1$ is methoxy, ethoxy, or benzyloxy; $R^2$ is methyl or ethyl, optionally substituted with one or more halo; and $R^3$ is phenyl or naphthyl.

5. The composition of claim 1 wherein $R^1$ is methoxy, ethoxy, methyl, or ethyl; $R^2$ is methyl or ethyl, optionally substituted with one or more halo; and $R^3$ is phenyl or naphthyl; wherein none of $R^1$, $R^2$, and $R^3$ are identical to each other.

6. The composition of claim 1 wherein $R^1$ is methoxy, ethoxy, or benzyloxy; $R^2$ is $CF_3$; and $R^3$ is phenyl or naphythyl.

7. The composition of claim 1 wherein $R^1$ is methoxy, $R^2$ is $CF_3$, and $R^3$ is phenyl.

8. The composition of claim 1 wherein the composition comprises the compound of formula I or salt thereof in at least a 20:1 ratio of R:S or S:R stereochemistry.

9. The composition of claim 1 wherein the composition comprises the compound of formula I or salt thereof in at least a 99:1 ratio of R:S or S:R stereochemistry.

10. The composition of claim 1 comprising a salt of the compound of formula I with a cation of formula 12:

12

11. The composition of claim 7 comprising a salt of the compound of formula I with a cation of formula 12:

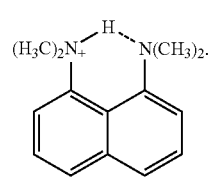

12

* * * * *